United States Patent
Sanghvi et al.

(10) Patent No.: US 8,788,958 B2
(45) Date of Patent: Jul. 22, 2014

(54) MODELING, MONITORING, AND ANALYSIS OF COMPUTER SERVICES

(75) Inventors: Ashvinkumar J Sanghvi, Sammamish, WA (US); Baelson B Duque, Seattle, WA (US); Thomas F Theiner, Sammamish, WA (US)

(73) Assignee: Microsoft Corporation, Redmond, WA (US)

( * ) Notice: Subject to any disclaimer, the term of this patent is extended or adjusted under 35 U.S.C. 154(b) by 953 days.

(21) Appl. No.: 11/755,939

(22) Filed: May 31, 2007

(65) Prior Publication Data

US 2008/0301574 A1 Dec. 4, 2008

(51) Int. Cl.
| | |
|---|---|
| *G06F 3/048* | (2013.01) |
| *G06F 3/06* | (2006.01) |
| *G06F 3/0484* | (2013.01) |
| *G06F 17/30* | (2006.01) |
| *G06F 3/01* | (2006.01) |
| *G06F 19/24* | (2011.01) |
| *G06F 19/26* | (2011.01) |

(52) U.S. Cl.
CPC .......... *G06F 3/067* (2013.01); *G06F 3/0484* (2013.01); *G06F 17/30905* (2013.01); *G06F 17/30572* (2013.01); *G06F 19/24* (2013.01); *G06F 19/26* (2013.01)
USPC ............ 715/771; 715/734; 715/736; 715/738

(58) Field of Classification Search
CPC . G06F 3/067; G06F 3/0484; G06F 17/30905; G06F 17/30572; G06F 17/3076; G06F 19/24; G06F 19/26

USPC ......... 715/733, 734, 736, 738, 739, 771, 790, 715/793, 804, 810, 853, 854, 969
See application file for complete search history.

(56) References Cited

U.S. PATENT DOCUMENTS

| | | | | |
|---|---|---|---|---|
| 5,276,789 A | * | 1/1994 | Besaw et al. | 345/440 |
| 5,471,399 A | * | 11/1995 | Tanaka et al. | 716/11 |
| 5,483,631 A | | 1/1996 | Nagai et al. | |
| 5,793,974 A | * | 8/1998 | Messinger | 709/224 |
| 5,812,750 A | | 9/1998 | Dev et al. | |
| 5,893,083 A | | 4/1999 | Eshghi et al. | |
| 5,958,012 A | * | 9/1999 | Battat et al. | 709/224 |

(Continued)

OTHER PUBLICATIONS

"Task Manager Overview", available at least as early as May 3, 2007, retrieved at <<http://www.microsoft.com/resources/documentation/windows/xp/all/proddocs/en-us/taskman_whats_there_w.mspx?mfr=true>>, Microsoft Corporation, 2007, pp. 1-2.

(Continued)

*Primary Examiner* — Nicholas Augustine
(74) *Attorney, Agent, or Firm* — Jim Sfekas; Kate Drakos; Micky Minhas

(57) ABSTRACT

Computer services and other computer entities may be monitored and evaluated by using a model that defines the services and relationships between the services. The model may be used during discovery for finding entities and creating instances of the entities and instances of the relationships between entities. After discovery, data may be collected and stored in a database by monitoring or instrumenting the entity. Analysis of the data may include tracking performance and monitoring the health of a service or other entity. The relationships may be used to graphically display various entities in many useful manners, including graphical representations of the health of various entities.

19 Claims, 6 Drawing Sheets

(56) References Cited

U.S. PATENT DOCUMENTS

| | | | |
|---|---|---|---|
| 5,991,708 A | 11/1999 | Levine et al. | |
| 6,151,023 A | 11/2000 | Chari | |
| 6,225,999 B1* | 5/2001 | Jain et al. | 715/734 |
| 6,347,336 B1* | 2/2002 | Song et al. | 709/223 |
| 6,714,976 B1* | 3/2004 | Wilson et al. | 709/224 |
| 6,885,387 B1* | 4/2005 | Machida | 715/736 |
| 6,885,641 B1* | 4/2005 | Chan et al. | 370/252 |
| 6,983,317 B1 | 1/2006 | Bishop et al. | |
| 7,360,158 B1* | 4/2008 | Beeman | 715/705 |
| 2002/0113816 A1* | 8/2002 | Mitchell et al. | 345/734 |
| 2003/0046390 A1* | 3/2003 | Ball et al. | 709/224 |
| 2003/0140139 A1 | 7/2003 | Marejka et al. | |
| 2003/0146929 A1* | 8/2003 | Baldwin et al. | 345/733 |
| 2005/0028158 A1 | 2/2005 | Ferguson et al. | |
| 2005/0055641 A1* | 3/2005 | Machida | 715/734 |
| 2005/0060663 A1 | 3/2005 | Arkeketa et al. | |
| 2005/0071482 A1* | 3/2005 | Gopisetty et al. | 709/229 |
| 2005/0114174 A1 | 5/2005 | Raden et al. | |

OTHER PUBLICATIONS

"Super Task Manager", available at least as early as May 3, 2007, retrieved at <<http://www.superlogix.net/taskmanager.htm>>, Superlogix Team, 2002-2005, p. 1.

"Task Commander 2.5", available at least as early as May 3, 2007, retrieved at <<http://pcwin.com/Utilities/System_Utilities/Task_Commander/index.htm,>>, PCWin Download Centre, 1995-2007, pp. 1-2.

* cited by examiner

MODELING, MONITORING, AND ANALYSIS OF COMPUTER SERVICES

BACKGROUND

Computer services are functions that are performed by a computing device. In many cases, computer services may be operating system functions, network communication functions, database management functions, or other operations that are generally performed continually and may be used by different devices or applications.

Many services may have an interface by which an administrator may interact with the service, including setting various parameters and monitoring the activities of the service. Network and system administrators may have a difficult or confusing time analyzing and diagnosing disparate software and hardware components when the interrelated components have problems.

SUMMARY

Computer services and other computer entities may be monitored and evaluated by using a model that defines the services and relationships between the services. The model may be used during discovery for finding entities and creating instances of the entities and instances of the relationships between entities. After discovery, data may be collected and stored in a database by monitoring or instrumenting the entity. Analysis of the data may include tracking performance and monitoring the health of a service or other entity. The relationships may be used to graphically display various entities in many useful manners, including graphical representations of the health of various entities.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
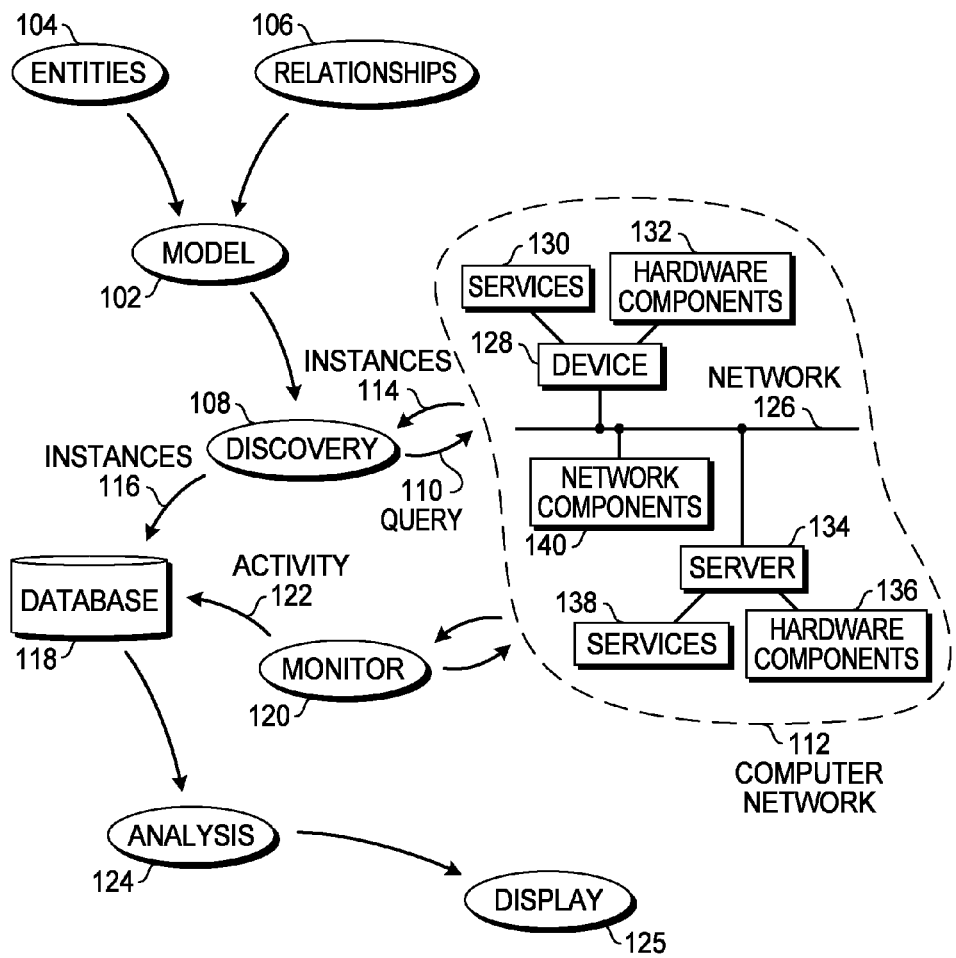
FIG. 1 is a diagram of an embodiment showing a system for monitoring and displaying computer activity and status.

A cohesive and integrated view of various computer-related items may be tracked and displayed by using a model built with relationships. By discovering and tracking instances of the entities and the relationships defined in the model, information relating to the entities may be displayed in meaningful and useful manners.

Entities may be defined for concrete objects, such as hardware components, but also for non-physical entities such as software components or services. Additionally, entities may be defined for abstract entities, such as subnets, computer clusters, services that are supplied within a specific location, or any other abstract entity. In many cases, entities may be defined that encompass a group of software services, hardware devices, or other components that may be monitored and managed as a single entity.

The model may include various entities that may be tracked in a computer system or a network of computer systems. When an entity is discovered, the model may be traversed to efficiently find other entities and define relationships between the entities. The entities and their relationships may be stored in a database. Any trackable item may be an entity, depending on the embodiment. For example, hardware components, software components, services, network devices, computer systems, and other items may be entities that are tracked and monitored. In many cases, abstract entities may be used to monitor and manage groups of other entities or components.

After an entity is discovered, an entity may be monitored to collect activity data about the entity. In some cases, an entity such as a computer service may be instrumented with code or other modifications so that the service may automatically report various activities. In other cases, a monitoring agent may be used to track activities related to the entity.

The activity data may be analyzed in many different manners, such as determining a status for the entity as well as determining an overall health assessment. In many cases, an entity's status may incorporate status or data from related entities. For example, the health of an entire system may be aggregated from multiple entities that are related to and make up the system.

The entities and their relationships may be displayed using many different formats and used for different purposes. A holistic view of a specific entity may be displayed with the entity status, the status of the entity's components, and those entities that interface with the entity. The view may use the relationships established in the original model and built into the database for composing and rendering the views.

Specific embodiments of the subject matter are used to illustrate specific inventive aspects. The embodiments are by way of example only, and are susceptible to various modifications and alternative forms. The appended claims are intended to cover all modifications, equivalents, and alternatives falling within the spirit and scope of the invention as defined by the claims.

Throughout this specification, like reference numbers signify the same elements throughout the description of the figures.

When elements are referred to as being "connected" or "coupled," the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by an instruction execution system. Note that the computer-usable or computer-readable medium could be paper or another suitable medium upon which the program is printed, as the program can be electronically captured, via, for instance, optical scanning of the paper or other medium, then compiled, interpreted, of otherwise processed in a suitable manner, if necessary, and then stored in a computer memory.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

When the subject matter is embodied in the general context of computer-executable instructions, the embodiment may comprise program modules, executed by one or more systems, computers, or other devices. Generally, program modules include routines, programs, objects, components, data structures, etc. that perform particular tasks or implement particular abstract data types. Typically, the functionality of the program modules may be combined or distributed as desired in various embodiments.

FIG. 1 is a diagram of an embodiment 100 showing a system for monitoring and displaying computer activities and status. Embodiment 100 is one system by which status of computer related items may be discovered, monitored, and displayed.

A model 102 may be created that is composed of entities 104 and relationships 106 between the entities. The model 102 may be used during the discovery, monitoring, and displaying processes to relate various entities with other entities.

The entities 104 may include any type of item that may be tracked. Such items may include computer systems as well as hardware or software components of a system.

Trackable items may include various hardware devices attached to or part of a computer system or network may have parameters that may be tracked. For example, trackable parameters may include processor and memory utilization, storage device response time, network interface usage, or any other parameter for a computer system. In another example, a network routing device may track number of packets, load factor, transmission errors, or other parameters. Each type of hardware device or component may have different trackable parameters.

Other trackable items may include software, services, or other functions provided by a device or system. For example, a network server device may provide DNS, DHCP, and other network infrastructure services to several devices attached to a network. Each service may have trackable parameters as well as relationships to other services or devices. For example, a SQL database service may have various performance parameters as well as relationships to other devices or services that use the SQL database service.

In some embodiments, a trackable item may be an abstract item that is made up of other entities. For example, an administrator may wish to monitor a group of print services that are used by a particular department in a company. An entity may be defined as a collection of print services so that the group of services may be managed as a single item.

A discovery mechanism 108 may send queries 110 over a computer network 112 to determine instances 114 of the various entities and relationships. The discovery mechanism 108 may use the model 102 to efficiently and quickly crawl the network 112 and locate entities and relationship.

The network 112 may include a network backbone 126 to which is attached a device 128 that may have various services 130 and hardware components 132. In many cases, a service 130 may be provided or consumed by a device 128. The services 130 may include operating level services, network communication services, software applications, utility services, interfaces, or any other software component or hardware function that may be tracked or monitored.

A server device 134 may also have hardware components 136 as well as services 138. Network components 140 may also act as entities or be composed of entities that may be tracked or monitored.

The discoverer 108 may crawl the network or an individual device to determine instances of entities to be tracked. In some embodiments, the discovery, monitoring, and display functionality of embodiment 100 may operate on a single computer system and may be used to track the various software and hardware components of a system.

In other embodiments, the embodiment 100 may track and monitor entities of which computer devices or servers are merely a component. For example, a large web service may use multiple web servers, multiple backend database servers, and various network management devices to provide web services to large volumes of users. In such an example, some services or entities may span multiple devices and multiple instances of some entities may be present.

After discovery 108, the instances 116 may be stored in the database 118. The instances 116 may include entity instances as well as relationship instances. An entity instance may be stored in the database 118 and have activity data 122 associated with it from the monitoring system 120. A relationship instance may be used during analysis 124 and display 125 to link various entity instances together.

The monitoring system 120 may collect data about the various entity instances. In some cases, the monitoring system 120 may use instrumentation to monitor the activity of an entity and in other cases, a separate monitoring service or application may collect activity data.

Instrumentation is a mechanism by which additional functionality may be attached to a software component so that data may be collected and sometimes transferred to another location. In some cases, such instrumentation may store data directly into the database 118 while in other case, such instrumentation may send messages that include data to a monitoring system 120. Any data collection mechanism may be used by the monitoring system 120 to collect data regarding the various entities.

In some embodiments, a monitoring system may create monitoring agents that are tailored to track specific instances of an entity. For example, a specific instance of a service operating on a specific server may be tracked or monitored by a service that intercepts messages sent by the service. Such a monitor may be adapted to operate on a very specific instance of the service.

The analysis mechanism 124 may perform any type of analysis on the database 118. In some cases, analysis may consist of summarizing, collating, or organizing data. In other cases, various statistics may be generated from raw data. In still other cases, qualitative summaries of activities may be defined. In an example of such a case, the health of a service may be qualified as Excellent, Good, Poor, and Bad.

In some cases, the analysis may use relationships between entity instances to aggregate data, to calculate summary factors, or to perform other analyses. For example, an entity instance may be comprised of other entity instances that are joined by relationship instances. The health of a first entity instance may be determined by evaluating the health of the entity instances to which the first entity instance is related.

The display function 125 may display the various entity instances, relationships, and data in any conceivable format. Examples of displays that use relationship instances to display various entity instances and data associated with the entity instances are discussed later in this specification.

Figure 2:
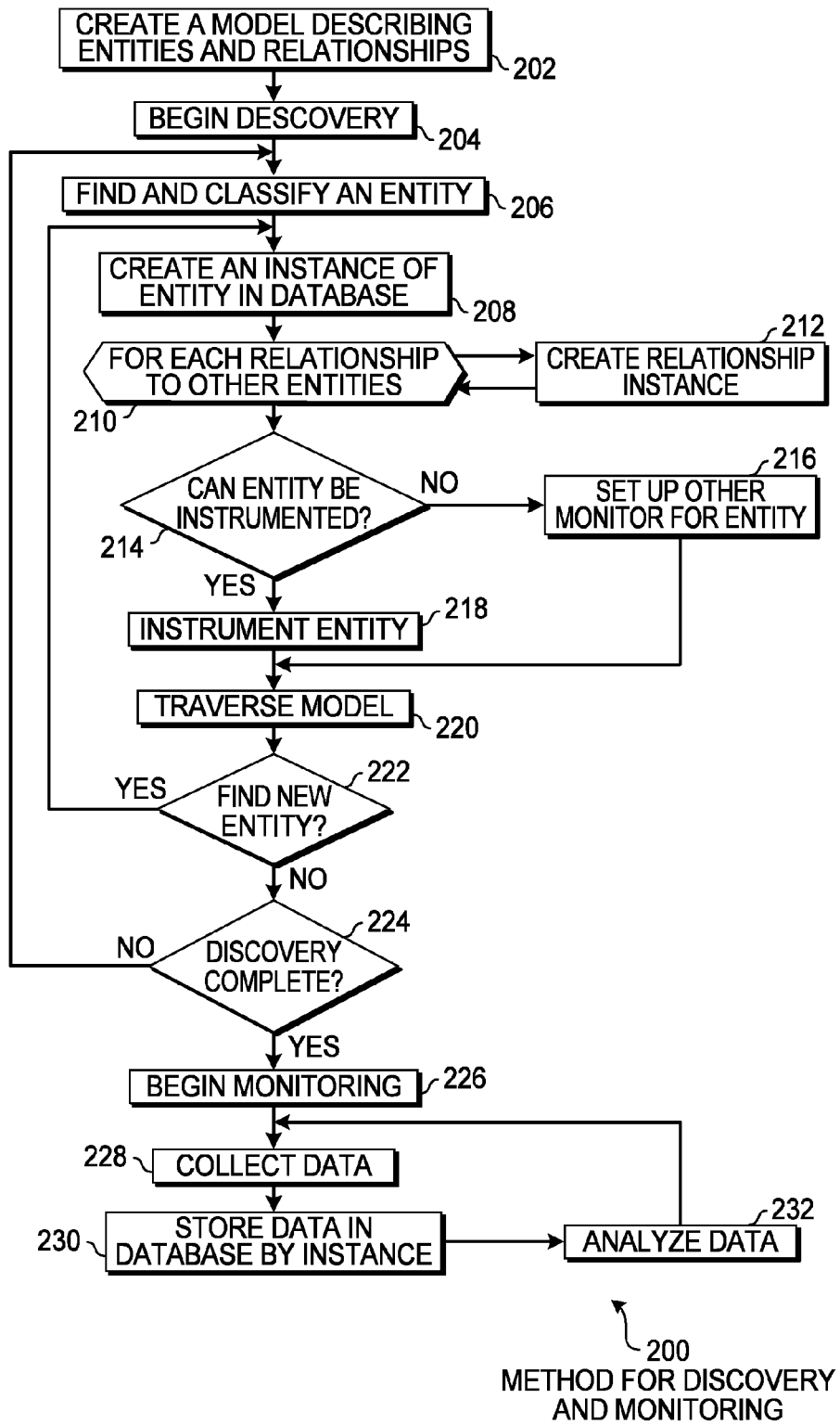
FIG. 2 is a flowchart illustration of an embodiment showing a method for discovery and monitoring various computer entities.

FIG. 2 is a flowchart illustration of an embodiment 200 showing a method for discovery and monitoring. Embodiment 200 illustrates one method by which entities and their relationships may be discovered, stored, and monitored. In some cases, an entity instance may be instrumented to facilitate monitoring. Other embodiments may use different sequences, steps, techniques, or mechanisms for discovery, storing, and monitoring entity instances.

A model is created in block 202 that describes entities and relationships. The model may describe various relationships between entities. In some cases, an entity may have one instance, while in other cases, an entity may have multiple instances. In some models, relationships may be unidirectional, bidirectional, parent/child, not specify a relationship type, or have some other type of relationship.

Each embodiment may have a different model that may be directed at the particular entities that are to be tracked and described in the level of detail appropriate for the tracking system.

Discovery begins in block 204.

An entity is found and classified in block 206. In some cases, a crawler or other mechanism may crawl a device, network, or other system to locate various entities. For example, a network crawler may send out a broadcast message across a local area network and receive one or more responses from other devices on the network. Such devices may be a starting point for a discovery mechanism.

An entity may be classified based on the model of block 202. When the entity is classified, an instance of the entity may be created in the database in block 208. Classification may involve matching the object discovered with an appropriate entity of the model. In some cases, a classification routine may determine that a single object may be several different entities, and a further investigation may include analyzing the relationships of each entity with the relationships discovered for the object to determine more precisely which classification to assign to the object.

In many cases, an entity may be an abstract entity that contains an item that may be discovered. When the item is discovered, various entities that may contain the item may be evaluated to determine if the item may indicate that a larger entity may exist that contains the item. Further discovery of other items may result in the discovery of a larger or abstract item. The model and the relationships within the model may be traversed to identify larger or abstract entities.

The discovery process may use any potential mechanism to discover and recognize an item. In some cases, discovery may occur over various layers of a network. For example, a layer 2 or 3 discovery may occur by sending a broadcast request over a network for any devices. Another example may be sensing layer 7 application communications across a network and determining the presence of a specific application. Still another example may be to locate a device and query the device to determine which services are being hosted by the device.

When the entity has relationships according to the model of block 202, for each relationship that exists with other entity instances in block 210, a relationship instance is created in block 212.

If the entity cannot be instrumented in block 214, a monitor is setup to detect activity or parameters for the entity in block 216. Otherwise, the entity is instrumented in block 218. Various embodiments may use different techniques or mechanisms for instrumenting or otherwise collecting activity and performance data for an entity. Each entity may have a particular design or other characteristics that may enable one method or mechanism more appropriate than another, and such methods or mechanisms may vary greatly between entities and embodiments.

In many cases, an entity instance may be monitored using a combination of instrumentation and a monitoring agent. In other cases, a customized monitoring agent may be created for the specific instance of an entity. In some cases, a single monitoring agent or service may collect activity data, performance data, availability data, or other data about two or more instances of an entity. Some embodiments may have a monitoring service able to monitor and collect data from different types of entities and different instances of each entity type.

The model may be traversed in block 220 to search for new entities in block 222. If a new entity is found in block 222, the process returns to block 208.

The model may be traversed from one entity to another by examining the relationships that an entity may have with other entities in the model. Based on the relationships, a discovery process may search for the second entity type. In many cases, the model may be used to determine an appropriate mechanism for searching for the related entity. For example, if an entity is related to another entity through a network connection, a discovery process may search over a network for a type of device or service.

If discovery is not complete in block 224, the process may return to block 206.

Monitoring may begin in block 226. Data is collected in block 228 and stored in the database by the particular entity instance in block 230.

Monitoring and data collection may be performed in many ways. Instrumented services or entities may automatically send data to a data collection application or the database itself. In other cases, a monitoring or alert system may monitor an entity and detect certain activities or parameters. Each embodiment may use different methods and mechanisms for data collection and monitoring.

The data may be analyzed in block 232. In some cases, each piece of incoming data may be analyzed or processed. In other cases, an analysis operation may be performed on a group of data on a periodic basis or as requested.

Figure 3:
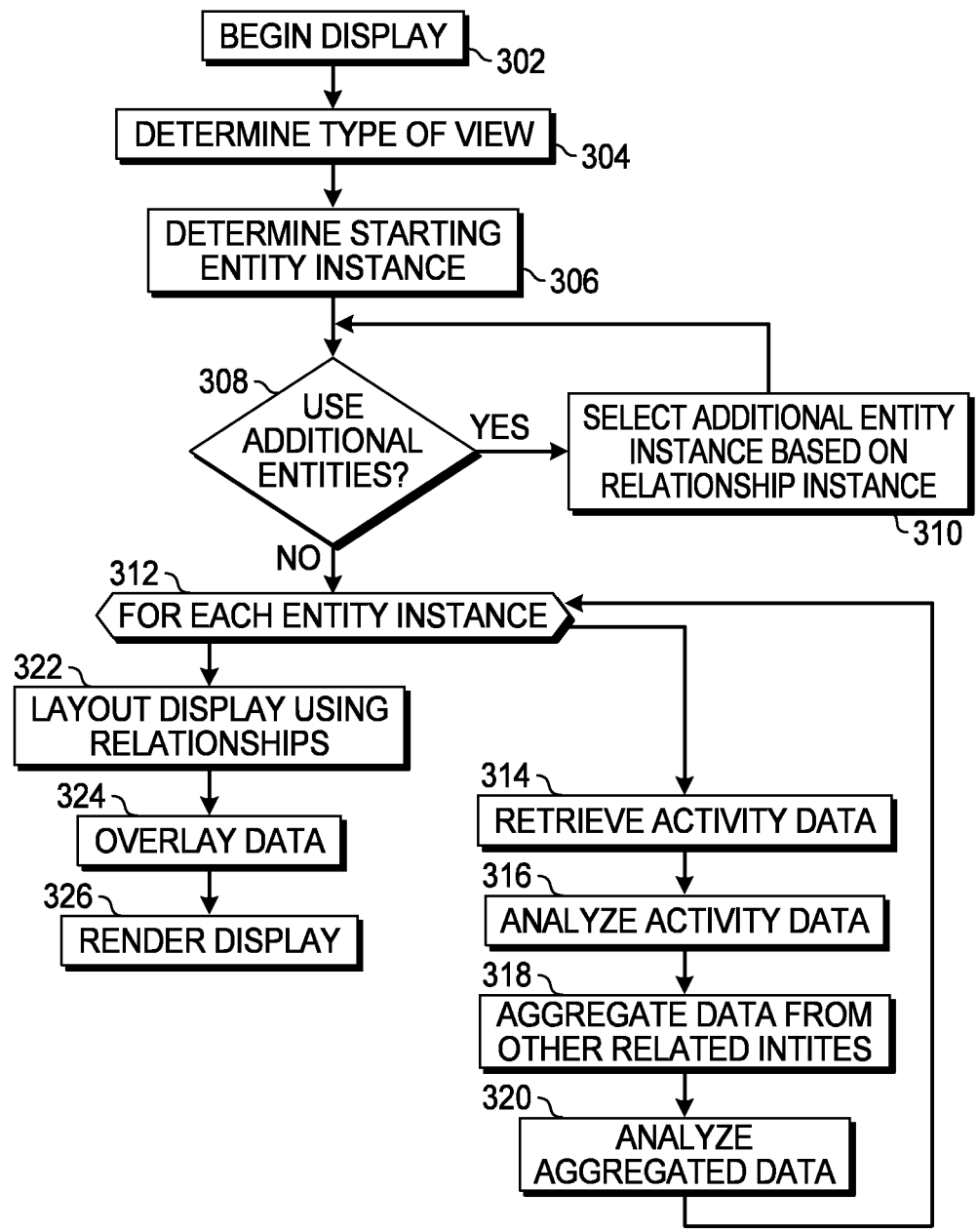
FIG. 3 is a flowchart illustration of an embodiment showing a method for analyzing and displaying data.

FIG. 3 is a flowchart illustration of an embodiment 300 showing a method for analyzing and displaying data. Embodiment 300 is merely one example of a method that creates a display based on various entities and the relationships between the entities. Analysis may be performed on activity data for one entity instance or on several related entity instances. Embodiment 300 is an example of analysis that may be performed as part of a display process. Other embodiments may perform data analysis on a periodic basis prior to preparing to display a portion of the data.

The display process may begin on block 302.

A type of view may be selected in block 304. Various embodiments may have different types of views available for a user to select. For example, one view may highlight a particular entity and the entities from which the first entity is composed. Such a view may be an 'inside-out' view. Another example may be an 'outside-in' view that shows entities outside a particular entity and the relationships between the various entities.

A relationship view may show the various relationships from one entity type to other entities, including peer to peer relationships, client/server relationships, parent/child relationships, host/guest relationships, or other types of relationships.

A transactional view may emphasize transactional data between two or more entities. A transactional view may give specific information regarding data or other communications between a pair of devices or throughout a network or portion of a network.

Some views may display configuration and availability of various entities and related entities.

Health alerts and performance views may show a health status of various related devices. In some such views, a problem with one entity may cause a problem with a related device. By displaying the related devices and statistics or health evaluation of the entities, a user may be able to diagnose problems between entities or among entities.

Many views may be used to communicate various monitoring, operational, and configuration parameters about entities. For example, icons, popup windows, summary statistics, or other information may be presented with various other data about the entities. Some embodiments may include interactive features that may enable an administrator or user to 'drill down' into more details within a view. For example, selecting an icon for an entity may enable a user to view transactions that occurred with the entity or view detailed statistics about the entity. Some examples of different displays or views are shown later in this specification.

In many views, a starting entity may be selected in block 306. A view may include other entities in block 308, and each of the additional entities may be selected based on a relationship instance in the database.

For each entity instance in block 312, activity data may be retrieved in block 314 and analyzed in block 316. In some cases, the analysis of block 316 may be to summarize the activity data into a single statistic, while in other cases, complex analysis generating multiple statistics may be performed.

In some cases, data from other related entities may be aggregated in block 318 and analyzed in block 320. For example, a health status may be determined by aggregating the health status of a first entity's component entities. Thus, the health status of each related entity may be determined and the health status of the first entity may be the summation or worst case of the health status of the various components.

After evaluating each instance in block 312, the display view may be laid out using relationship instances in block 322. Data may be overlaid in block 324 and the display rendered in block 326.

The layout and organization of each view may be different based on the type of view, the number of related entities, and the types of relationships defined between entities. In many cases, those entities that have relationship instances defined between the entities may be displayed in a visual manner that shows the relationships.

Figure 4:
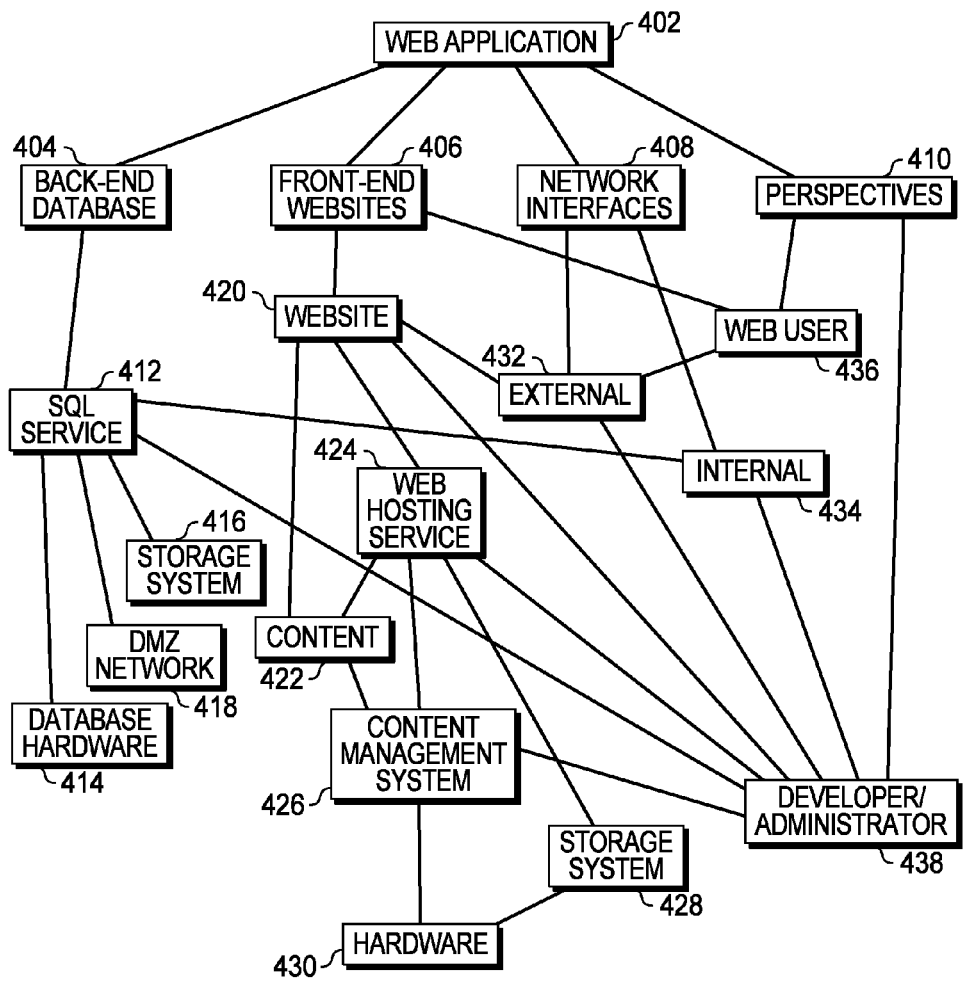
FIG. 4 is a diagram of an example of an embodiment of a model for web services.

FIG. 4 is a diagram illustration of an embodiment 400 showing an example model of a web application. Embodiment 400 is merely an example of various entities and relationships between entities that may be used in discovery, analysis, and display of performance and status data for various entities. Embodiment 400 may be the basis for the example displays illustrated in subsequent Figures.

The model of embodiment 400 contains various entities and relationships between the entities. The model was selected to highlight one way a model may be constructed. Other models may have different types of entities, various types of relationships, and model different types of systems.

A web application 402 may have a backend database system 404, front end websites 406, and various network interfaces 408. Additionally, perspective entities 410 may be used to define various perspectives or ways to view data within the database. In this example, some entities may relate to specific hardware or software systems, while other entities, such as the perspective entities, may be ephemeral and are used to give various summaries or views of the various entities.

The backend database 404 may have one or more SQL services 412. Each SQL service 412 may have a database hardware entity 414, a storage system entity 416, and a DMZ or de-militarized zone network entity 418.

In each use of a model, some of the entities may not be found and thus instances of those entities may not be stored in a database. In some cases, a relationship may be defined so that multiple instances of an entity may exist, while in other cases one instance may be permitted. Some relationships may provide a definite relationship, such as the SQL service 412 will operate on the database hardware entity 414. Thus, whenever a SQL service 412 is encountered, a database hardware entity 414 will also be encountered. In another example, a web application may have several backend databases, and each of the backup databases may have several SQL services supporting the databases.

The frontend websites entity 406 may have one or more instances of a website 420, which may have content entity 422 and a web hosting service entity 424. The content entity 422 and web hosting service entity 424 may have a relationship between them and both may be related to a content management system 426 and a storage system entity 428. Both the content management system 426 and storage system 428 may be related to a hardware entity 430.

The network interface entity 408 may be comprised of one or more external network interface entities 432 and one or more internal network interface entities 434. The external network interface entity 432 may be related to the website entity 420, while the internal network interface entity 434 may be related to the SQL service entity 412.

The perspectives entity 410 may have a web user entity 436 that is related to the external network interface entity 432 and the frontend website entity 406. The web user perspective entity 436 may be used to generate performance metrics and views that are particular to a web user. Similarly, a developer or administrator perspective entity 438 may be related to the website entity 420, the SQL service entity 412, the web hosting service entity 424, and the content management system entity 426.

Figure 5:
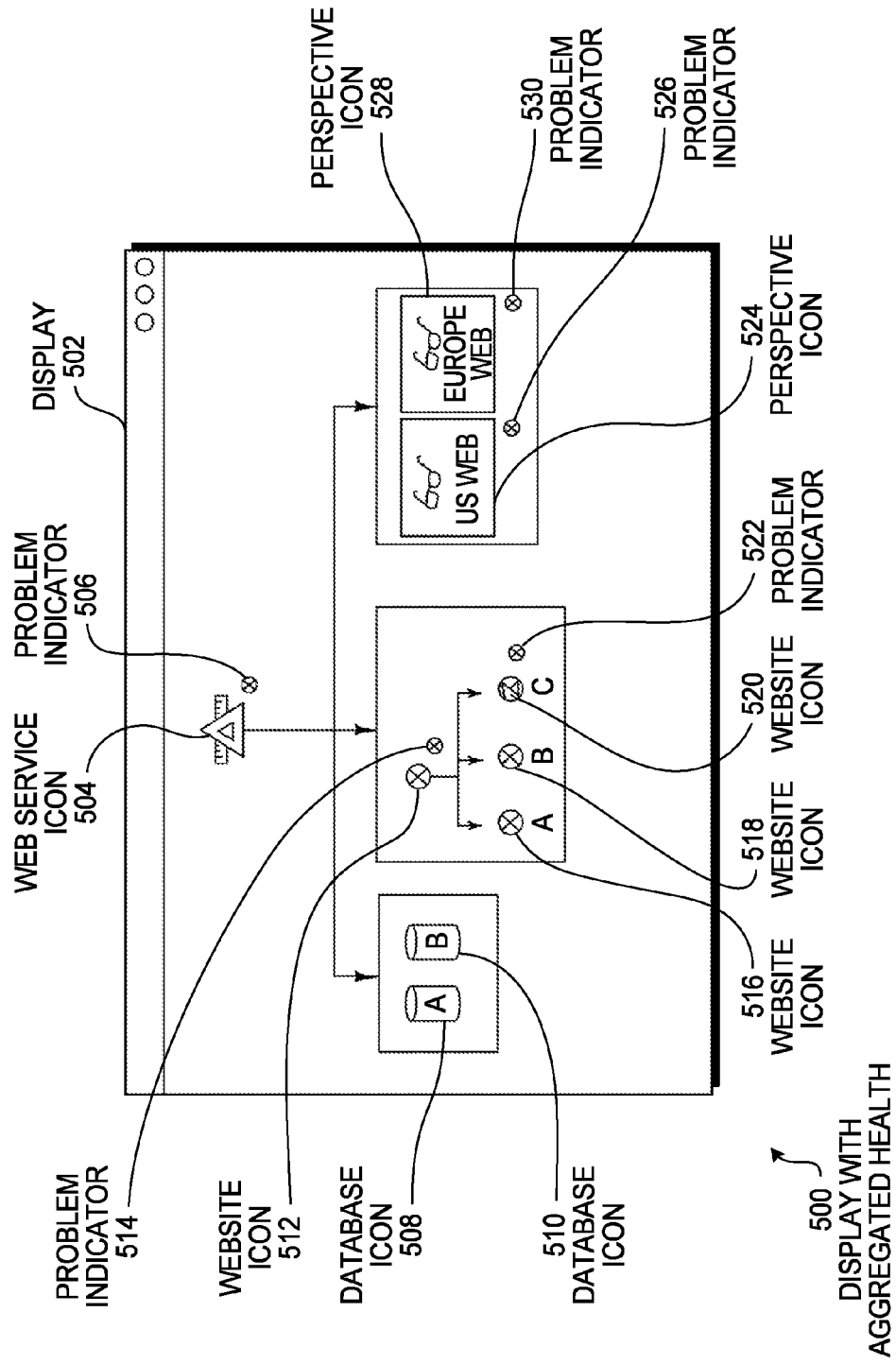
FIG. 5 is a diagram of an example of a display with aggregated health of computer elements.

FIG. 5 is a diagram illustration of an embodiment 500 illustrating a display with aggregated health for an entity instance. The embodiment 500 illustrates a top-down view of a web service instance with various entity instances and relationships that make up the web service instance. The display 502 may be a graphical display as used on a computer terminal.

A web service icon 504 is shown with a problem indicator 506. The problem indicator 506 may be used to summarize the health of the web service instance. The web service is made up of two databases, as shown by the database icons 508 and 510, as well as a hierarchy of websites.

The hierarchy of websites is shown by a website icon 512, from which three web site icons 516, 518, and 520 are children. The main website icon 512 has a problem indicator 514 as well as child website icon 520 has problem indicator 522.

The perspective icons 524 and 528 similarly have problem indicators 526, and 530, respectively.

An administrator or network operator who may view the display 502 may be able to determine that a problem exists with the overall web service. From the display, many of the components that make up the web service appear to be operating properly, however, the website icon 520 appears to have a problem. A user of the display may begin focusing attention to the website of icon 520 in order to troubleshoot the apparent problem.

Figure 6:
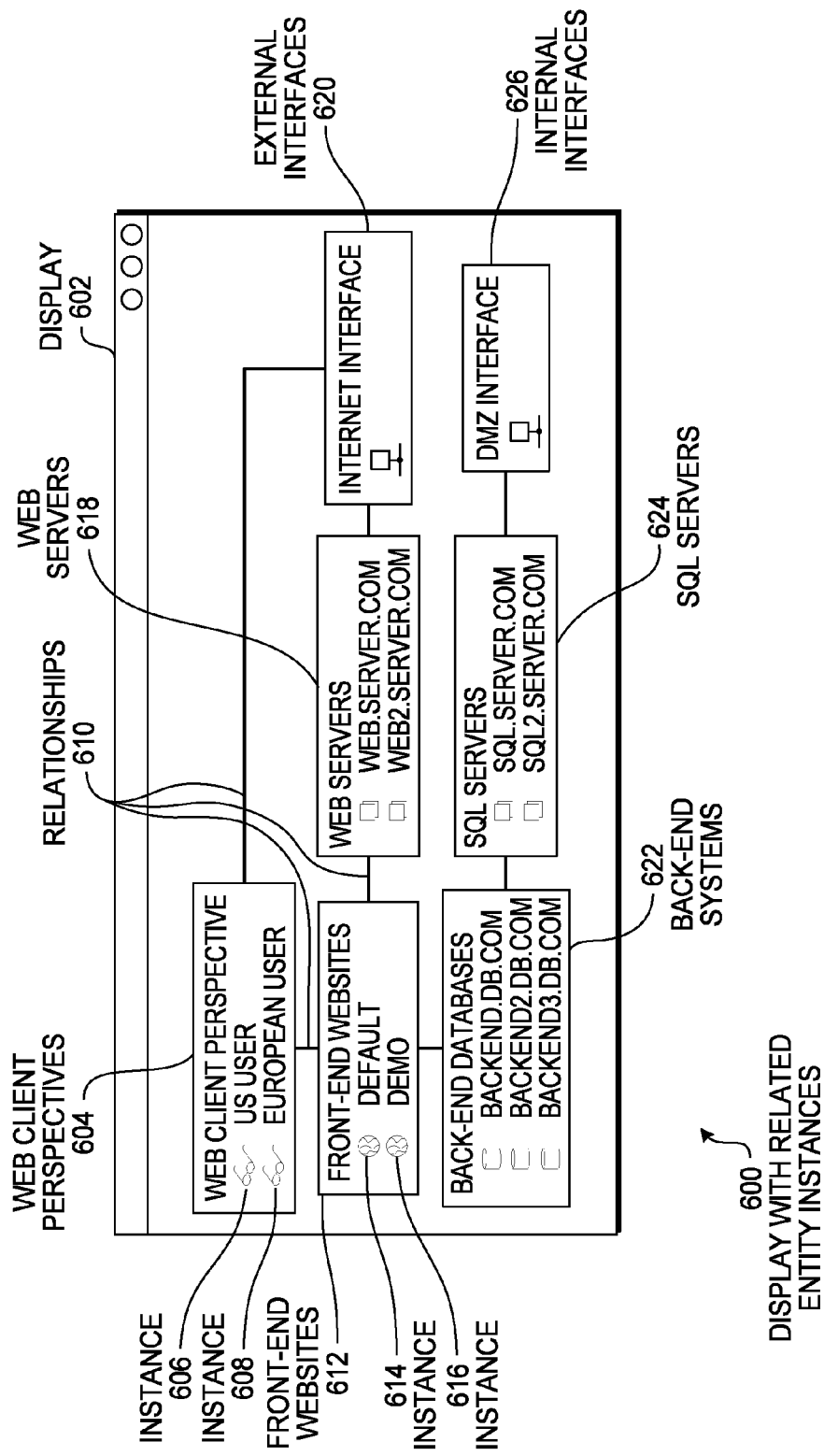
FIG. 6 is a diagram of an example of a display with related entity instances.

FIG. 6 is a diagram illustration of an embodiment 600 showing a second view of various entity instances and relationship instances between the entity instances. Embodiment 600 is an overall view of a group of web service related entities as grouped by type with relationships between the types.

The display 602 may contain a group of web client perspectives 604 that may contain instances 606 and 608. The web client perspectives 604 have various relationships 610. For example, the web client perspectives 604 may be directly related to the front end websites 612 that has instances 614 and 616. The front end websites 612 may have a relationship to web servers 618, which has a relationship to network interfaces 620. Similarly shown, the front end websites 612 may be related to backend databases 622, which may be related to SQL servers 624, which is in turn related to the DMZ interfaces 626.

Within each classification of entities, one or more instances may be present. The view of embodiment 600 may enable an administrator or other user to get high level view of a web services system and the various instances that make up the system.

In many embodiments, the display 602 and display 502 of embodiment 500 may be interactive graphical user interfaces. Some embodiments may enable a user to click on an instance of an entity to switch to a view that highlights the entity or enables the user to perform specific tasks or display data relating to the entity. In some cases, popup windows may be displayed with detailed information. Other cases may enable a user to launch a detailed monitoring or administration application to enable the user to change the configuration of an entity instance. Still other cases may allow a user to view detailed listings of various transactions that have occurred or that make up a specific calculated statistic.

Many different displays may be rendered using collected data and relationships between various entities in a model. For example, a display may be used to illustrate entities that make up a first entity. Such a display may be an 'inside-out' display. Another display may illustrate a hierarchical view of entities, such as a display that shows subordinate entities or superior entities. Other displays may show an entity from the vantage point of several other entities, or the connections or relationships through which pass data or other items. Some displays may show a time series of events for a single entity or a group of entities.

In some displays, data from activities monitored for an entity or relationship may be shown in various forms. In some cases, raw data may be shown. In other cases, the data may be analyzed and summarized into various forms before presentation, including value judgments and qualitative assessments.

The foregoing description of the subject matter has been presented for purposes of illustration and description. It is not intended to be exhaustive or to limit the subject matter to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments except insofar as limited by the prior art.

What is claimed is:

1. A method comprising:
accessing information of entities in a model comprising said entities and relationships between said entities;
searching a computer network to discover an object;
matching the object to more than one entity defined in said model;
determining a set of relationships between the object and the entities in the model;
analyzing the relationships for each entity in the model that matches the object, with the set of relationships for the object, to determine that the object should be classified as a first entity in the model;
classifying said object as a first entity instance of the first entity;
traversing said model to discover and communicate with a second entity instance of a second entity and a relationship instance of a first relationship between said first entity instance and said second entity instance;
monitoring entity instances for activities;
storing said activities in a database;
displaying a graphical representation of said first entity instance, said second entity instance, and said relationship instance, said graphical representation being based on said model, and further including perspective icons and problem indicators associated with each instance.

2. The method of claim 1 further comprising:
analyzing said activities to create summary data; and
displaying said summary data in said graphical representation.

3. The method of claim 2, said summary data comprising a health status.

4. The method of claim 3, said health status for said first entity instance comprising a health status for said second entity instance.

5. The method of claim 1, said entity comprising at least one of a group composed of:
a computer service;
a computer device;
a component of a computer device;

a network component;
an interface;
a subnet;
a group of said entities; and
a cluster of said computer devices.

6. The method of claim 1 further comprising instrumenting said first entity instance by placing code on the first entity instance allowing the first entity instance to provide activity and performance data.

7. A computer readable storage medium comprising computer executable instructions adapted to perform the method of claim 1.

8. A system comprising:
 a database adapted to store entity instances, relationship instances, and activity information about said entity instances, said entity instances and said relationship instances being based on a model of entities and relationships between said entities, said entities comprising computer services;
 a discoverer adapted to search a computer device to discover and communicate with a first of said instances and traverse said model to discover said relationship instances and said entity instances, said first of said instances being matched with at least one entity instance defined in said model, said discoverer further adapted to classify said first of said instances to a stored entity instance when said first of said instances matches more than one entity instance defined in said model, by analyzing said relationships between each of the more than one entity instance that was matched;
 a monitor adapted to collect said activity information; and
 a display adapted to show a plurality of said entity instances and said relationship instances, said display including icons illustrating relationships between said plurality of entity instances and a problem indicator associated with each of the instances.

9. The system of claim 8, said entities further comprising at least one of a group composed of:
 a computer service;
 a computer device;
 a component of a computer device;
 a network component;
 an interface;
 a subnet;
 a group of said entities; and
 a cluster of said computer devices.

10. The system of claim 8 further comprising:
 an analyzer adapted to analyze said activities.

11. The system of claim 10, said analyzer adapted to determine a health status for at least one of said entities.

12. The system of claim 11, said display adapted to show said health status through said problem dicators.

13. The system of claim 11, said health status being an aggregation of health status of a plurality of said entities.

14. A method comprising:
 instrumenting a first entity instance by placing code on the first entity instance allowing the first entity instance to provide activity and performance data;
 collecting activity and performance data relating to said first entity instance and a second entity instance, said first entity instance being related to said second entity instance to form a relationship instance; said first entity instance, said second entity instance, and said relationship instance being based on a model having entities and relationships between entities, said entities comprising computer services, said data being collected by communicating with said first entity instance and said second entity instance, said first entity instance being matched with at least one entity defined in said model;
 storing said data in a database; and
 displaying said first entity instance, said second entity instance, and said relationship instance in a graphical representation including perspective icons and problem indicators.

15. The method of claim 14 further comprising:
 analyzing said data to create summary data; and
 displaying said summary data in said graphical representation.

16. The method of claim 15, said summary data comprising a health status.

17. The method of claim 16, said health status for said first entity instance comprising a health status for said second entity instance.

18. The method of claim 14, said entity further comprising at least one of a group composed of:
 a computer service;
 a computer device;
 a component of a computer device;
 a network component;
 an interface;
 a subnet;
 a group of said entities; and
 a cluster of said computer devices.

19. A computer readable storage medium comprising computer executable instructions adapted to perform the method of claim 14.

* * * * *